United States Patent
Newton et al.

(10) Patent No.: US 10,004,816 B2
(45) Date of Patent: *Jun. 26, 2018

(54) X-RAY IMAGING CONTRAST MEDIA WITH LOW IODINE CONCENTRATION AND X-RAY IMAGING PROCESS

(71) Applicant: GE HEALTHCARE AS, Oslo (NO)

(72) Inventors: Ben Newton, Amersham (GB); Mikkel Thaning, Oslo (NO); Dirk-Jan in't Veld, Oslo (NO); Karina Langseth, Oslo (NO); Paul Michael Evans, Amersham (GB)

(73) Assignee: GE HEALTHCARE AS, Oslo (NO)

( * ) Notice: Subject to any disclaimer, the term of this patent is extended or adjusted under 35 U.S.C. 154(b) by 821 days.

This patent is subject to a terminal disclaimer.

(21) Appl. No.: 14/371,350

(22) PCT Filed: Jan. 10, 2013

(86) PCT No.: PCT/EP2013/050342
§ 371 (c)(1),
(2) Date: Jul. 9, 2014

(87) PCT Pub. No.: WO2013/104690
PCT Pub. Date: Jul. 18, 2013

(65) Prior Publication Data
US 2015/0190533 A1    Jul. 9, 2015

(30) Foreign Application Priority Data
Jan. 11, 2012   (EP) .................................. 12150785

(51) Int. Cl.
*A61K 49/04* (2006.01)
*A61B 6/03* (2006.01)
*A61B 6/00* (2006.01)

(52) U.S. Cl.
CPC .......... *A61K 49/0438* (2013.01); *A61B 6/032* (2013.01); *A61B 6/481* (2013.01); *A61K 49/0433* (2013.01)

(58) Field of Classification Search
None
See application file for complete search history.

(56) References Cited

U.S. PATENT DOCUMENTS

| | | | |
|---|---|---|---|
| 4,887,604 A | 12/1989 | Shefer et al. | |
| 5,993,780 A * | 11/1999 | Almen | A61K 49/0433 424/9.452 |
| 7,713,517 B2 | 5/2010 | Annapragada et al. | |
| 8,815,210 B2 * | 8/2014 | Wistrand | A61K 49/0438 424/9.1 |
| 2001/0004395 A1 | 6/2001 | McCrory et al. | |
| 2006/0072800 A1 | 4/2006 | Deman et al. | |
| 2008/0310582 A1 | 12/2008 | Flohr et al. | |
| 2009/0263326 A1 | 10/2009 | Karathanasis et al. | |
| 2010/0322868 A1 * | 12/2010 | Thaning | A61K 49/0433 424/9.452 |
| 2013/0004433 A1 | 1/2013 | Glogard et al. | |

FOREIGN PATENT DOCUMENTS

| | | |
|---|---|---|
| EP | 0108638 B1 | 7/1986 |
| EP | 2550022 A1 | 1/2013 |
| EP | 2802357 A1 | 11/2014 |
| EP | 1742669 B1 | 7/2015 |
| JP | 2007-533737 A | 11/2007 |
| JP | 5947784 B2 | 7/2016 |
| WO | 1991/001149 A1 | 2/1991 |
| WO | 98/20499 A1 | 5/1998 |
| WO | 2005/087272 | 9/2005 |
| WO | 2005107820 A1 | 11/2005 |
| WO | 2007/051739 | 5/2007 |
| WO | 2009/008734 | 1/2009 |
| WO | 2010/079201 | 7/2010 |
| WO | 2011/051387 | 5/2011 |
| WO | 2011/117236 | 9/2011 |
| WO | 2013/104690 A1 | 7/2013 |

OTHER PUBLICATIONS

Second Written Opinion regarding SG Application No. 11201403963X, dated Jun. 13, 2016, 7 pages.
Raininko, et.al. Acta Radiologica 1990 Dk, vol. 31, No. 3, 1990, pp. 309-314.
Jynge, et.al. Investigative Radiology 1993, vol. 28, No. 1, 1993, pp. 20-25.
Jynge, et.al. Investigative Radiology 1995, vol. 30, No. 3, 1995 pp. 173-180.
Elmstahl, et.al. Academic Radiology, vol. 11, No. 11 Nov. 1, 2004, pp. 1219-1228.
Nyman Gefasschirugie: Zeitscrift Fur Vaskulare Und Endovaskulare Chirurgie, vol. 16, No. 7, Sep. 3, 2011 pp. 469-480.
PCT/EP2013/050342 ISRWO dated Mar. 21, 2013.
Oksendal Acta Physical Scand 1991, S599 pp. 149-156.
GE Today, Oct. 2010, p. 2-3.
Office Action Received for Russian Patent Application RU2014125447/15(041393), dated Sep. 26, 2017, 16 Pages (8 Pages of English Translation + 8 Pages Official Copy).

\* cited by examiner

*Primary Examiner* — Michael G Hartley
*Assistant Examiner* — Melissa J Perreira
(74) *Attorney, Agent, or Firm* — Wood IP LLC

(57) ABSTRACT

The present invention relates to X-ray examinations and to the improvement of patient safety during such. More specifically the invention relates to X-ray diagnostic compositions having low concentrations of iodine and an optimized amount of electrolytes. The invention further relates to methods of X-ray examinations wherein a body is administered with an X-ray diagnostic composition comprising a low concentration of iodine and irradiated with a radiation dose.

19 Claims, 7 Drawing Sheets

A) FBP, Aorta: 318 (Muscle SD 13.7)

B) FBP, Aorta: 407 (Muscle SD 21.5)

C) ASiR 60%, Aorta: 406 (Muscle SD 14.2)

D) VEO, Aorta: 407 (Muscle SD 7)

A) FBP, Aorta: 345 (Muscle SD 16)

B) FBP, Aorta: 312 (Muscle SD 23.8)

C) ASIR 60%, Aorta: 312 (Muscle SD 15.4)

D) VEO, Aorta: 323.4 (Muscle SD 7.8)

A) FBP, Aorta: 345 (Muscle SD 16)

B) FBP, Aorta: 347 (Muscle SD 22.9)

C) ASIR 60%, Aorta: 345 (Muscle SD 15.1)

D) VEO, Aorta: 348 (Muscle SD 8.2)

A) FBP, Liver: 129 (± 16.6)

B) FBP, Liver: 164 (± 25.6)

C) ASIR 60%, Liver: 184 (± 17.3)

D) VEO, Liver: 167 (± 19)

A) FBP, Liver: 142 (± 17.3)

B) FBP, Liver: 134 (± 29.4)

C) ASIR 60%, Liver: 134 (± 17.4)

D) VEO, Liver: 140 (± 9.3)

A) FBP, Liver: 142 (± 17.3)

B) FBP, Liver: 121 (± 23.7)

C) ASiR 80%, Liver: 123 (± 15.6)

D) VEO, Liver: 124 (± 9.5)

X-RAY IMAGING CONTRAST MEDIA WITH LOW IODINE CONCENTRATION AND X-RAY IMAGING PROCESS

This application is a filing under 35 U.S.C. 371 of international application number PCT/EP2013/050342, filed Jan. 10, 2013, which claims priority to EP application number 12150785.9 filed Jan. 11, 2012, the entire disclosure of which is hereby incorporated by reference.

FIELD OF THE INVENTION

The present invention relates to X-ray compositions having low concentrations of iodine and an optimized amount of electrolytes. Particularly, the invention provides a composition comprising Ioforminol and providing a low concentration of iodine. The invention further relates to methods of X-ray examinations using such composition. In a particular embodiment a body is administered with the X-ray composition of the invention and irradiated with a reduced radiation dose.

BACKGROUND OF THE INVENTION

All diagnostic imaging is based on the achievement of different signal levels from different structures within the body so that these structures can be seen. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast or definition between a body structure or region of interest and its surroundings the higher the conspicuity or quality of the images and the greater their value to the physician performing the diagnosis. Moreover, the greater the contrast the smaller the body structures that may be visualized in the imaging procedures, i.e. increased contrast can lead to increased discernable spatial resolution and conspicuity.

The diagnostic quality of images is strongly dependent on the inherent noise level in the imaging procedure, and the ratio of the contrast level to the noise level or definition between contrast and noise can thus be seen to represent an effective diagnostic quality factor for diagnostic images. Achieving improvement in such a diagnostic quality factor has long been and still remains an important goal whilst keeping the patient safe, especially from excessive radiation. In techniques such as X-ray imaging one approach to improving the diagnostic quality factor has been to introduce contrast enhancing materials formulated as contrast media into the body region being imaged.

Thus in X-ray early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade mark Gastrografen™), ionic dimers such as ioxaglate (marketed e.g. under the trade mark Hexabrix™), non-ionic monomers such as iohexol (marketed e.g. under the trade mark Omnipaque™), iopamidol (marketed e.g. under the trade mark Isovue™), iomeprol (marketed e.g. under the trade mark Iomeron™) and the non-ionic dimer iodixanol (marketed under the trade mark Visipaque™).

The most widely used commercial non-ionic X-ray contrast agents such as those mentioned above are considered safe for clinical use. Contrast media containing iodinated contrast agents are used in more than 20 million of X-ray examinations annually in the USA and the number of adverse reactions is considered acceptable. However, there is still a need for improved methods for X-ray, and CT images, providing increased safety and high-quality images. This need is more apparent in patients/subjects with pre-existing diseases and conditions or immature/low renal function. This is because certain diseases and low renal function increase the chance of adverse reactions to injected iodinated contrast media. Pre-existing diseases of concern include lung disease, kidney disease, heart disease, liver disease, inflammatory disease, autoimmune disease and other comorbidities e.g. metabolic disorders (diabetes, hyperlipidaemia, hyperinsulinaemia, hypercholestraemia, hypertriglyceridaemia and hypertension), cardiovascular disease, peripheral vascular disease, atherosclerosis, stroke and congestive heart failure. Furthermore a subject's age is important since a greater number of adverse events are reported in the elderly, while immature renal function, as can be found in young children and infants, can also lead to prolonged circulation of contrast media and a greater number and intensity of adverse reactions.

The risk of adverse events is not limited to the effects of contrast media. Radiation associated with CT accounts for about 70-75% of the total ionizing radiation from diagnostic imaging. While these levels of radiation are well below those that cause deterministic effects (for example, cell death), there is concern that they may be associated with a risk of stochastic effects (such as cancer, cataracts and genetic effects). Those at greatest risk for developing radiation exposure-related cancer later in life are children and women in their 20s, and according to Hall E J. Ped Radiol 2002; 32: 225-7 are children 2-10 times more sensitive to radiation than adults. Approximately 33% of all paediatric CT examinations are performed in children in the first decade of life, with 17% in children at or under the age of 5 years. Exposure to radiation at an early age carries a risk because organs and tissues in children are more sensitive to the effects of radiation than those of an adult and they have a longer remaining life expectancy in which cancer may potentially form. Brenner D et al. N Engl J Med 2007; 357: 2277-83 reports that the risk of death from cancer exists after only a single CT scan, and although low, this risk is considerably higher for children and young people. In addition, the current prevalence of CT makes it more likely that children will receive a higher cumulative lifetime dose of medically related radiation than those who are currently adults.

Since such contrast media are conventionally used for diagnostic purposes rather than to achieve direct therapeutic effect or provide a patient benefit, it is generally desirable to provide contrast media having as little as possible effect on the various biological mechanisms of the cells or the body as this will lead to lower toxicity and lower adverse clinical effect. The toxicity and adverse biological effects of iodinated contrast media are contributed to by the components of the formulation medium, e.g. the solvent, carrier, buffers or chelators as well as the contrast agent itself and its components such as ions for the ionic contrast agents, and also by its metabolites.

The major contributing factors to the toxicity of the contrast medium are identified as the chemotoxicity of the iodinated contrast agent structure and its physicochemistry, especially the osmolality of the contrast medium and the ionic composition or lack thereof of the contrast medium formulation. Desirable characteristics of an iodinated contrast agent have been considered to be low toxicity of the compound itself (chemotoxicity), low osmolality of the contrast medium, high hydrophilicity (solubility) and a high iodine content, frequently measured in mg iodine per ml (mg I/ml) of the formulated contrast medium for administration. The iodinated contrast agent must also be completely soluble in the formulation medium, usually an aqueous medium, and remain in solution during storage and administration.

The osmolalities of the commercial products, and in particular of the non-ionic compounds, is acceptable for most media containing dimers and non-ionic monomers although there is still room for improvement. In coronary angiography for example, injection into the circulatory system of a bolus dose of contrast medium may cause severe side effects. In this procedure, immediately after injection contrast medium rather than blood flows through the system for a short period of time, and differences in the chemical and physiochemical nature of the contrast medium and the blood that it replaces can cause undesirable adverse effects such as arrhythmias, prolongation of the QT interval of the heart's electrical cycle, reduction in cardiac contractive force, reduction in oxygen carrying capacity of blood cells and tissue ischemia of the organ in which high levels of contrast media are present. Such effects are seen in particular with ionic contrast agents where chemotoxic and osmotoxic effects are associated with hypertonicity of the injected contrast medium. Contrast media that are isotonic or slightly hypotonic with the body fluids are particularly desired. Hypoosmolar contrast media have low renal toxicity which is particularly desirable.

In patients with acute renal failure, nephropathy induced by contrast medium remains one of the most clinically important complications of the use of iodinated contrast medium. Aspelin, P et al, The New England Journal of Medicine, Vol. 348:491-499 (2003) concluded that nephropathy induced by contrast medium may be less likely to develop in high risk patients when iodixanol, a hypoosmolar agent made isoosmolar with blood due to the addition of plasma electrolytes, is used rather than a low-osmolar, non-ionic contrast medium. These findings have later been reinforced by others, showing that Iodine contrast media osmolality is the key driver of contrast induced nephrotoxicity (CIN) and contrast media induced acute kidney injury.

The portion of the patient population considered as high-risk patients is increasing e.g. due to higher expected average age. To meet the need for continuous improvement of in vivo X-ray diagnostic agents for the entire patient population, there is a continuous drive in finding X-ray contrast agents and methods for x-ray imaging wherein the patient safety is optimized.

To keep the injection volume of the contrast media low it has been desirable to formulate contrast media with high concentration of iodine/ml, and still maintain the osmolality of the media at a low level, preferably below or close to isotonicity. This thinking corresponds to the notion that a higher iodine concentration may provide better diagnosis. The development of non-ionic monomeric contrast agents and in particular non-ionic bis(triiodophenyl) dimers such as iodixanol (EP 108638) has provided contrast media with reduced osmotoxicity. This has allowed contrast with effective iodine concentration to be achieved with hypotonic solution, and has even allowed correction of ionic imbalance by inclusion of plasma ions while still maintaining the contrast medium at the desired osmolality, e.g. as for Visipaque™.

However, to reduce the risk of adverse events, especially in susceptible subjects, to improve patient safety and to reduce costs, there is now a desire to reduce the amount (volume and iodine dose) of X-ray contrast media administered to patients undergoing X-ray examinations.

WO 2009/008734 of GE Healthcare AS discloses a new class of compounds and their use as X-ray contrast agents. The compounds are dimers containing two linked iodinated phenyl groups. The bridge linking the two iodinated phenyl groups is a straight C3 to C8 alkylene chain optionally substituted by one to six —OH or OCH3 groups. A range of compounds are covered by the general formula (I) of the application and many specific compounds are suggested. Compound I, which is one specific dimeric X-ray contrast agent, falling within the formula I of WO2009/008734, given the International Non-proprietary name Ioforminol, has been found by the applicant to have particularly favourable properties. Compound I is 5,5'-((2-hydroxypropane-1,3-diyl)bis(formylazanediyl))bis(N1,N3-bis(2,3-dihydroxypropyl)-2,4,6-triiodoisophthalamide).

SUMMARY OF THE INVENTION

The applicant has now surprisingly identified a new X-ray diagnostic composition providing improved patient safety. The new composition which is useful as a contrast media in X-ray imaging comprises Ioforminol as the contrast agent, and provides a low concentration of iodine. A composition has been identified providing an optimised amount of salts.

Hence, in a first aspect the invention provides an X-ray composition comprising Ioforminol and a pharmaceutically acceptable carrier or excipient, wherein the composition comprises an iodine concentration of 10-200 mg I/ml and a sodium ion concentration of 70-120 mM. The iodine present in the composition is mainly from Ioforminol, which includes six iodine atoms per molecule.

BRIEF DESCRIPTION OF THE DRAWINGS

The FIGS. 1 to 6 show iodine contrast enhancement by measuring the mean X-ray attenuation values within circular region of interests, using compositions of Ioforminol of different concentrations, at different tube voltage energies and using different software to reduce noise. For the FIGS. 1 to 3 the region of interest is the aorta, and for the FIGS. 4-6 the region of interest is the liver.

DETAILED DESCRIPTION OF THE PREFERRED EMBODIMENTS

Figure 1:
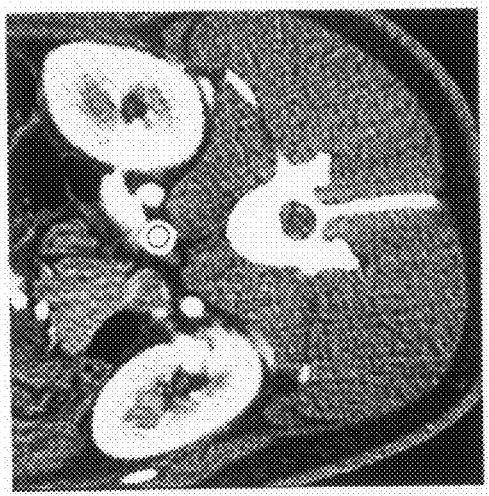
FIG. 1 shows images A to D using Ioforminol of 320 mg I/ml and 200 mg I/ml, and tube voltage energies of 120 and 80 KVp according to Table 1.
Figure 1:
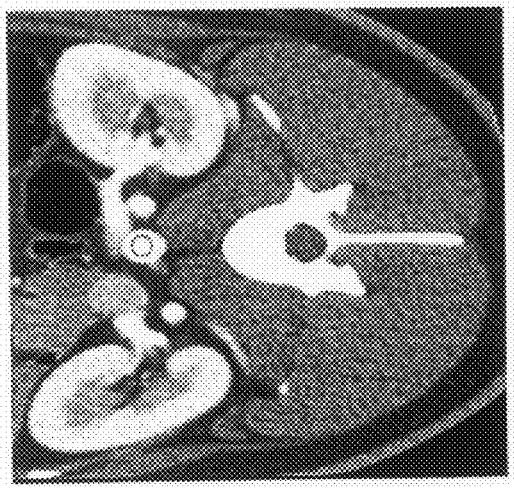
Figure 1:
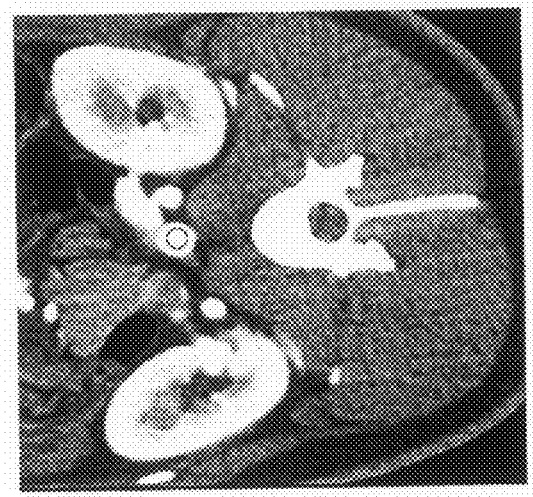
Figure 1:
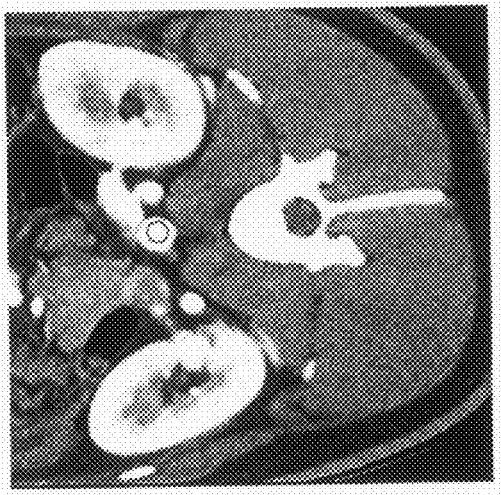

The applicant has tested and surprisingly found that contrast media concentration, i.e. the iodine concentration, can be reduced to unexpectedly low levels without compromising the contrast to noise and/or quality of the obtained X-ray images. Further, to our surprise, for the new X-ray contrast agent Ioforminol, when formulated in a composition with as little iodine as 10-200 mg I/ml, the sodium ion content can be increased to as much as 70-120 mM of sodium ions. The sodium ion concentration is preferably above 72 mM, such as above 75 mM. When the iodine concentration is reduced, the sodium ion addition is increased and vice versa, hence when the iodine concentration is at the maximum level 200 mg I/ml the sodium concentration is around 72 mM. More preferably, the composition comprises an iodine concentration of 10-170 mg I/ml and a sodium ion concentration of 72-120 mM, and most preferably above 72 mg I/ml.

In one embodiment, when the composition comprises 10-200-mg I/ml, the composition of the invention further comprises a calcium ion concentration of 0.5-1.3 mM, and more preferably 0.5-1.1 mM.

Hence, the invention provides an x-ray composition comprising a physiologically tolerable aqueous carrier medium with dissolved therein the contrast agent Ioforminol, characterised in that the iodine concentration of the composition is 10-200 mg I/ml and in that the carrier medium has dissolved therein a physiologically tolerable sodium compound providing a sodium ion concentration of 70-120 mM, and optionally further a physiologically tolerable calcium compound providing a calcium concentration of 0.5-1.3 mM.

In a preferred embodiment, the composition of the invention comprises an iodine concentration of 40-170 mg I/ml and a concentration of sodium ions of 80-107 mM. In addition, the composition preferably comprises a calcium concentration of 0.6-1.0 mM. In this embodiment, specific compositions encompassed comprise for example 40, 80, 120 or 160 mg I/ml. For these compositions the maximum sodium and calcium content would preferably be as provided below, all having osmolalities of about 290 mOsm/kg:

|  | Sodium conc. | Calcium conc. |
|---|---|---|
| Ioforminol 40 mg I/ml | 109 mM | 0.9 mM |
| Ioforminol 80 mg I/ml | 100 mM | 0.9 mM |
| Ioforminol 120 mg I/ml | 91 mM | 0.8 mM |
| Ioforminol 160 mg I/ml | 82 mM | 0.7 mM |

In one embodiment, the composition of the invention comprises an iodine concentration of 80-130 mg I/ml and a concentration of sodium ions of 88-100 mM. In addition, the composition preferably comprises a calcium concentration of 0.7-0.9 mM.

In another embodiment, the composition of the invention comprises an iodine concentration of up to 100 mg I/ml and a concentration of sodium ions of 95 mM or more. In this embodiment, the composition preferably comprises a calcium concentration of about 0.8 mM or more in addition.

In a specific embodiment of the invention the composition comprises Ioforminol providing an iodine concentration of about 160 mg I/ml, a sodium ion concentration of about 82 mM and a calcium ion concentration of about 0.7 mM.

In another specific embodiment of the invention the composition comprises Ioforminol providing an iodine concentration of about 200 mg I/ml, a sodium ion concentration of about 75 mM, and most preferably of 73 mM, and a calcium ion concentration of 0.6 mM.

It is desirable to make up the composition's tonicity by the addition of cations found in human plasma so as to reduce the toxicity contribution that derives from the imbalance effects following bolus injection. In particular, addition of sodium and calcium ions to provide a contrast medium isotonic with blood for all iodine concentrations falling within the range of the invention is desirable and found obtainable. For X-ray diagnostic compositions given by bolus injection, e.g. in angiographic procedures, osmotoxic effects must be considered and preferably the composition should be isotonic with blood. For the composition of the invention the osmolality should be in the range of 160-320 mOsm/kg, preferably below 300 mOsm/kg and most preferably about 290 mOsm/kg which is the blood osmolality. With an iodine concentration of for example 120 mg I/ml, the sodium ion concentration should be about 90 mM, and the calcium ion concentration should be about 0.8 mM, to provide the preferred osmolality.

The ratio of sodium to calcium ion in the composition is in the range of 90-120, more preferably between 100-120 and most preferably about 116. This ratio has been found optimal, with the formulation having minimal adverse effects on the heart.

In a further embodiment, additional other electrolytes are included in the composition of the invention. Hence, the composition may include physiologically acceptable salts providing ions selected from the group of potassium and magnesium. In a preferred embodiment the composition further includes potassium ions in the range of 3.6-4.8 mM and/or magnesium ions in the range of 0.65-0.95 mM.

The X-ray composition of the invention is isotonic, it has a low concentration of iodine and a high concentration of sodium ions, and is a patient friendly formulation. Most other X-ray contrast media on the market are hypoosmolar and have no physiological electrolytes present. Visipaque™, comprising Iodixanol, are isotonic formulations in the formulations available. Visipaque™ is made isotonic with normal body fluids by additions of electrolytes. The concentrations of the electrolytes found needed for Ioforminol compared to those for Iodixanol, such as sodium, are however much higher, such as around 30% or higher at comparing concentrations of iodine.

Despite the close resemblance between Iodixanol and Ioforminol which differs structurally by only two methyl groups there is a surprisingly large difference in non-ideal behaviour in solution. By intermolecular interactions the contrast media molecules form clusters that are continuously formed and broken up and the average cluster size may be described by a formation/destruction equilibrium. Ioforminol has an increased tendency to form clusters and in water at high concentration an average size of 4 molecules per cluster is predominating, whereas Iodixanol under similar conditions have a mean cluster size of 2.5 molecules. As the concentration goes down the average cluster size decreases and at low concentrations clusters are no longer present for Iodixanol. The cluster size affects the osmolality of the solution and larger clusters are reflected in a lower osmolality. The non-ideal behaviour of high concentration solutions permits the addition of physiological electrolytes to achieve isotonicity. Surprisingly solutions with the novel lower concentrations of Ioforminol retain the non-ideal behaviour with 2-3 molecules per cluster and an osmolality deviating from the calculated ideal value. This non-ideal behaviour persistent also at low concentrations enables the addition of physiological electrolytes to the current formulations.

The mentioned cations may be provided in the form of salts with physiologically tolerable counter-ions, e.g. chloride, sulphate, phosphate, hydrogen carbonate etc., with anions found in plasma preferably being used. Chloride is preferably used as counter-ion. The pharmaceutically acceptable carrier is an aqueous solution, preferably pure water. The composition preferably further includes pharmaceutically acceptable excipients. Examples of such are Ethylenediaminetetraacetic acid (EDTA) and tris(hydroxymethyl)amino methane (TRIS). More specifically, the composition preferably includes either of TRIS, as a buffer, sodium calcium EDTA, as a chelating agent, sodium chloride and calcium chloride, for isotonic adjustment, hydrochloric acid and sodium hydroxide, for pH adjustment, in addition to water for injection as the carrier.

For X-ray diagnostic compositions which are administered by injection or infusion, the desired upper limit for the solution's viscosity at ambient temperature (20° C.) is generally about 30 mPas, however viscosities of up to 50 to 60 mPas and even more than 60 mPas are seen. With the low concentration of iodine in the composition of the invention the viscosity is below 10 mPas at 20° C., and this is even considerably lower at the lower end of the iodine concentration range. Hence, in a further embodiment the invention provides an X-ray composition comprising Ioforminol further having a viscosity below 10 mPas. For comparison a 320 mg I/ml composition of Ioforminol has a viscosity of 28 mPas (at 20° C.). Particularly, for a 160 mg I/ml composition of Ioforminol the viscosity is only 2.9 mPas (at 20° C.), and for a 200 mg I/ml composition the viscosity is 4.7 mPas (20° C.). Hence, the new low iodine concentration compositions of Ioforminol cause a reduction in viscosity down to about 15% of the high concentration compositions. Such low viscosity has the advantage that the composition is easy to administer and the administration can be done more quickly with a higher volume per time unit, particularly as the injection pressure needed is considerably lower than with compositions with higher viscosities. The lower viscosity enables a reduction in the needle- or catheter diameter down to about 63% of the original diameter without effecting flow rate or injection pressure. As a consequence a hand-held syringe can be used rather than an autoinjector. When thinner cannulas or catheters are used in the administration, this is reducing the size of the skin puncture from the needle-stick and there is hence less risk of extravasation, which is particularly favourably in pediatrics and for elderly patients, providing a more patient friendly contrast media administration.

The X-ray diagnostic composition can be administered by injection or infusion, e.g. by intravascular administration. In one embodiment, the X-ray diagnostic composition is administered as a rapid intravascular injection, in another embodiment it is administered as a steady infusion.

In one embodiment, the invention provides a composition dose, such as an x-ray diagnostic dose for administration, wherein the composition comprises an iodine concentration according to the invention, and wherein the total volume of the composition administered is between 1 and 250 ml. In one embodiment, the iodine dose volume for an adult is 1.5 ml/kg of the composition of the invention. For an adult of 75 kg the volume administered of a 160 mg I/ml concentration of the composition is preferably 100-120 ml, e.g. 113 ml providing an iodine dose of 18 g. If providing the Ioforminol composition from a vial of 100 ml, the iodine content for a 160 mg I/ml concentration is 16 g. This is a considerable reduction compared to other available contrast media. The most frequently used available concentration for x-ray contrast media is 300 mg I/ml. For the 160 mg I/ml composition of the invention, compared to a concentration of 300 mg I/ml there is a 47% reduction in the iodine content in a 100 ml vial. Compared to a concentration of 240 mg I/ml the reduction is 33%, while for a concentration of 400 mg I/ml the reduction is as much as 60%. Ioforminol can be prepared as outlined in WO 2009/008734. A general procedure is outlined on pages 16-20, and a specific method for preparation is provided in Example 1 of WO 2009/008734. The WO 2009/008734 application, with its description of a process for preparation is hereby incorporated by reference.

Ioforminol may exist in several isomeric forms due to chiral carbon atoms. In addition, the compound exhibits exo/endo isomerism due to the restricted rotation of the N—CO bond in the formyl function caused by the proximity of the bulk iodine atom. Compositions of both the enantiomerically pure compounds as well as mixtures of optical isomers are included.

By the compositions and methods of the invention, there are several objectives achieved. Considerable cost savings can be made by the reduction of costs by reducing use of higher concentration contrast media as to achieve Cost of Goods and raw material savings. Most importantly there are patient safety benefits through the combination of reduced iodine concentration and total dose of contrast media. The lower iodine concentration exposure is especially beneficial to patients with pre-existing disease, such as reduced heart and kidney function.

The iodine concentration of the X-ray composition has been found to be important as the composition, when administered to a body, replaces blood. By lowering the radiation dose of the X-ray tube i.e. by lowering tube voltage (kilo volt peak or kVp), i.e. the difference in potential between the cathode and anode, and administering low concentrations of iodine, the image quality, i.e. the contrast effect, has been found to actually be maintained or improved. This is because the attenuation value of iodinated enhancements is increased at a lower tube voltage as the dose of radiation has an average energy spectrum substantially corresponding to the k-edge of iodine, resulting in higher enhancement. Iodine HU values (Hounsfield Units) in the CT image are greater, i.e. the image quality is improved, at lower kVps because the average energy of the spectrum is closer to the k-edge of iodine (33.2 keV (kilo electron volts)) thus the increased attenuation coefficient of iodine at lower x-ray energies results in higher CT image HU values.

Hence, it is the actual concentration of iodine, that attenuate incident X-ray radiation, that is lowered, and not only the dose of iodinated contrast media (volume). As a consequence, if the volumes of injected iodinated contrast agent remain the same and the concentration of iodine based contrast agent is reduced, the total amount of injected iodinated contrast agent into the body will be reduced. Using the composition of the invention has benefits over just reducing the overall standard dose of diagnostic composition or reducing the rate of administration of this. The concentration of iodine has been found to be more important than the dose for image ability since the contrast media pushes the blood out of the way and i.e. displaces or replaces blood, so that it alone is "imaged". Since the overall contrast media dose is reduced because the contrast media concentration is reduced the dose of contrast agent is important for patient safety.

In a second aspect the invention provides a method of X-ray examination comprising administering to a body an X-ray composition comprising Ioforminol and a pharmaceutically acceptable carrier or excipient, wherein the composition comprises an iodine concentration of 10-200 mg I/ml and a sodium ion concentration of 70-120 mM, applying a radiation dose to the body, examining the body with a X-ray diagnostic device and compiling data from the examination.

In one embodiment, the radiation dose is reduced compared to standard doses. It has been found that when an imaging method combining use of the X-ray composition of the invention with irradiation with a reduced radiation dose, images are obtained with satisfactory, or event improved image quality.

In one embodiment the only purpose of the method of the invention is to obtain information. The method may include analysing the data. In another embodiment, the method further includes a step of comparing the obtained information with other information so that a diagnosis can be made. In one embodiment, the method for examination is a method of diagnosis or is an aid for diagnosis. The radiation dose is applied to the body, such as to a specific region of interest of the body.

Currently, X-ray/CT equipment algorithms only consider image quality and radiation dose as parameters when optimizing (i.e. lowering) radiation dose and/or improving image quality. Generally, the dose of radiation required to obtain a certain image quality in X-ray/CT scans can be reduced using advanced algorithms to reduce image noise associated with lower radiation exposure during the acquisition of images. In addition, applicant has now found that by decreasing the tube voltage, the amount of contrast material can be reduced to unexpectedly low levels by reducing the concentration without compromising image quality.

The method of the present invention preferably includes the use of the particular composition of ioforminol comprising a low concentration of iodine, and a high concentration of salts, in accordance with the first aspect, and combining this with a reduction in radiation dose and kVp, without compromising image quality and effective diagnosis. The method may furthermore include the use of advanced image reconstruction algorithms that are specifically designed to remove or reduce the soft-tissue noise resulting from the use of low radiation/low kVp scans.

Several techniques for achieving a reduction in the radiation dose during X-ray examinations, such as CT examinations, exist. One technique is to use low tube voltage. In one embodiment of this aspect, a polychromatic radiation spectrum is provided by tube voltages in the range of 60-150 kVp, such as 60-140 kVp, more preferably 70-120 kVp, even more preferably 70-90 kVp and most preferably 70-80 kVp. This will typically provide x-ray spectra of 30-140 keV (for 140 kVp tube voltage), more preferably 30-120 keV (for 120 kVp tube voltage), even more preferably 30-90 (for 90 kVp tube voltage) and most preferably 30-80 keV (for 80 kVp tube voltage). Hence, the tube voltage is most preferably at or below 80 kVp in special populations i.e. children and small adults. Accordingly, when the body has been administered with the composition of the invention, the x-ray/CT equipment is operated such that the body is irradiated with X-rays, preferably in accordance with CT, with a tube voltage as provided above. Today, the majority of abdominal CT scans are e.g. taken at 120 kVp or higher.

With the composition and method of the invention, this tube voltage, and accordingly the radiation dose, can be reduced as suggested without compromising on the image quality. Equivalent or better conspicuity, i.e. equal or higher contrast to noise ratio, of iodinated structures can be achieved when reducing the radiation dose, for instance from 140 kVp to 80 kVp or to values as low as 60 or 70 kVp. This is because the average energy of the polychromatic spectrum is closer to the k-edge of iodine (33.2 keV). The K-edge describes a sudden increase in the attenuation coefficient of X-ray photons just above the binding energy of the K shell electrons of the atoms interacting with the X-ray photons. The sudden increase in attenuation is due to photoelectric absorption/attenuation of the X-rays. Iodine has K shell binding energies for absorption/attenuation of X-rays of 33.2 keV, which is not necessarily close to the mean energy of most diagnostic X-ray beams. Thus, at lower photon energy more X-rays can be attenuated by iodine. Extrapolating such phenomena to contrast enhanced scanning procedures in the clinical setting, the use of low energy photons (i.e. low radiation), brighter images can be obtained. Alternatively, if less iodine is administered, equivalent image intensity could result. The balance between the low X-ray energy and the low amount (concentration of iodine) required to render images that are equivalent in quality and intensity as standard X-ray energy scans at normal or standard iodine concentrations, is of critical importance. Hence, in one embodiment of the method of the invention the dose of radiation applied has an average energy spectrum substantially corresponding to the k-edge of iodine.

In addition to reducing the radiation dose by lowering the tube voltage, other options are available. Any technique, including CT technology, hardware and algorithms, for reducing the X-ray radiation dose, combined with the administration of the composition of the invention, is encompassed by the method of the invention. CT equipment settings, i.e. exposure parameters such as x-ray tube current, slice thickness, pitch or table speed can be adjusted to reduce the radiation dose. CT technology including axial scanning may be used. In such technique there is no overlap of slices, without significant decrease in speed. Further, tube current (mA or milliampere) modulation may be performed, i.e. turning down the X-ray tube current when not needed, and in particular turning it down through thinner sections of the body or when bony structures are smaller or not present. Milliamperage represents a second control of the output of the X-ray tube. This control determines how much current is allowed through the filament on the cathode side of the tube. If more current (and heating) is allowed to pass through the filament more electrons will be available in the "space charge" for acceleration to the x-ray tube target and this will result in a greater flux of photons when the high voltage circuit is energised. Similar approaches using kVp modulation based on patient size are also envisaged as an additional method for infant, child or adult patient radiation dose reduction. In addition, a Garnet-based ceramic scintillator detector, which has a high temporal resolution, may be used. Such detectors provide more contrast from the same radiation dose. Further, such fast detectors can also accommodate dual-energy GSI (Gemstone Spectral Imaging) imaging from a single source (X-ray tube) by rapid kVp switching. Scanning with such Dual Energy CT (DECT) and using GSI processing, enables to obtain spectral information and the reconstruction of synthetic monochromatic images, such as between 40 and 140 keV. In one embodiment, the examination step of the method of the invention includes the use of DECT. Higher contrast is provided when using lower energy monochromatic DECT images, but due to reduced photon intensity such technique may suffer from higher noise levels. Software that improves image quality may further be used to suppress noise. Filtered back projection (FBP) and Adaptive Statistical Iterative Reconstruction (ASiR™), a reconstruction method that selectively sweeps noise from CT images, allow the radiation dose to be reduced with no change in spatial or temporal resolution.

Likewise: Iterative Reconstruction in Image Space (IRIS™), iDOSE, SAFIRE and Quantum Noise Filter reduce image noise without loss of image quality or detail visualization. More complex iterative techniques, such as model-based iterative reconstruction (MBIR), such as Veo™, may lead to further noise and dose reductions or better image quality. Hence, in a further embodiment, the examination step of the method of the invention includes operating the equipment such that scanning with DECT, optionally combined with noise suppression, is performed. Such noise suppression is preferably selected from ASiR and MBIR. Combining DECT with noise suppression, improved contrast to noise is achieved. Further, using DECT, with or without additional dedicated noise suppression methods, allows for the use of an X-ray diagnostic composition with a significantly reduced iodine concentration. For instance, scanning with DECT, e.g. at radiation doses of 21.8 mGy and 12.9 mGy, showed that a reduction of about 25% in the concentration of iodine, compared to standard 120 kV scans, is allowed for (EP2011/061843, Example 6). Using DECT and noise suppression the usable energy window is increased without compromising on image quality.

With any such technique for reducing noise, the radiation dose can be reduced and together with reduced iodine concentration, adult, child or infant patient safety is further enhanced. In a preferred embodiment, the method of the invention includes a step of noise reduction, preferably through advanced image reconstruction and/or image filtration methods. Such noise reduction is achieved by selecting and operating available software, and it is preferably selected from ASiR and MBIR (Veon™). Compared to standard Filter Back Projection, both ASiR and MBIR significantly improve the contrast to noise radio, also in studies with iodine contrast. In a preferred embodiment, MBIR (Veo™) is used in the method of the invention.

The radiation dose needed is dependent on the procedure, on the region of interest, and on the weight, and age, of the patient. Hence, in a preferred embodiment, the invention provides a method of X-ray examination comprising administration to a body a composition according to the first aspect, applying a reduced kVp and limited mAs (milliamperexsec exposure level) for reduced X-ray radiation dose, and examining the body with a diagnostic device and compiling data from the examination, wherein the method further includes a step of noise reduction through advanced image reconstruction means.

With the method of the invention the radiation dose of a standard CT of abdominal region may be reduced by up to 50% from an average of 8 mSv (milliSievert) or less, of CT of central nervous system (spine) by up to 50% from an average of 5 mSv, and CT of chest by up to 50% from an average of 7 mSv. With the method of the invention, using an X-ray diagnostic composition with an ultra-low concentration of iodine and advanced reconstruction software, the radiation dose can, depending on the type of reconstruction, be reduced by 10%, 20%, 30%, 40% or even 50%, 60%, 70% or even 80-90% compared to standard radiation doses, without compromising on the imaging quality. With the method of the invention, using the composition according to the first aspect, the dose settings can be reduced similarly, i.e. from standard 50 mAs to e.g. 25 mAs.

In a preferred embodiment, the invention provides a method of X-ray examination comprising administration to a body a composition according to the first aspect, irradiating the body with a reduced radiation dose, e.g. by using a tube voltage lower than 150 kVp, such as 80 kVp, and tube currents in the 5-1000 mA range, such as in the 5-700 mA range, or in the 5-500 mA range, and examining the body with a diagnostic device, and compiling data from the examination.

Optionally, but preferably, the examining of the body with a diagnostic device includes reconstructing the image using any reconstruction software and compiling data from the examination, using any image/data management system.

With the method of the invention it has been found that the image quality is at least maintained, good, or even improved compared to procedures wherein standard doses of radiation and standard concentrations of contrast agent are applied. Hence, by the methods and compositions of the invention the contrast to noise ratio is maintained, compared to standard methods and compositions, or even improved, to preserve or improve image quality. The CT attenuation value of iodinated enhancement is increased at a lower tube voltage, resulting in higher enhancement and/or maintained or better definition. The image quality, measured in Hounsfield Units (HU), obtainable by the method of the invention is typically 60-350 HU.

Image Quality (IQ) ranges for typical imaging procedures are e.g.:

Post Contrast Arterial Phase Density Measurements at regions of interests: Abdominal Aorta/Renal Artery/Kidney Cortex/Liver Parenchyma/Portal Vein/IVC=60-350 HU.

Post Contrast Venous Phase Density Measurements at various regions of interests: Abdominal Aorta/Renal Artery/Kidney Cortex/Liver Parenchyma/Portal Vein/IVC=80-350 HU.

The X-ray composition and the method of the invention may be used for the X-ray examination of different regions of interest, and for several types of indications. Examples are intra-arterial or intra venous administration of the X-ray composition for visualizing vascular structures, for visualising thoracic, abdominal neoplastic and non-neoplatic lesions, for indications related to head and neck, and for the evaluations of the periphery/body cavities.

In a third aspect the invention provides a method of X-ray examination comprising examining a body pre-administered with a composition according to the first aspect, comprising the method steps of the second aspect of the invention. This aspect includes the same features and fall-backs as the two first aspects of the invention.

In a fourth aspect the invention provides composition according to the first aspect, for use in a method of x-ray examination. In one embodiment, the use comprises administering the composition to a body, applying a reduced X-ray radiation dose to the body, examining the body with a diagnostic device and compiling data from the examination. This aspect includes the same features and fall-backs as the two first aspects of the invention.

The methods of the invention may further include a step of analysing the data.

The invention is illustrated with reference to the following non-limiting examples.

EXAMPLES

Example 1: Iodine Concentrations at 200 and 160 mg I/Ml, Decreased Radiation Dose and Advanced Reconstruction Techniques Maintain the Contrast-to-Noise Ratio (CNR) of Abdominal Contrast Enhanced CT Images in the Pig Three studies were carried out in two anaesthetized minipigs (abdominal maximum and minimum diameters approximately 36 cm and 20 cm, respectively). Minipigs were imaged on a Discovery CT 750 HD. Compositions of 160 mg I/ml and 200 mg I/ml Ioforminol were prepared. The 160 mg I/ml formulation included a sodium concentration of 82 mM and a calcium concentration of 0.9 mM. The 200 mg I/ml formulation included a sodium concentration of 73 mM and a calcium concentration of 0.8 mM. For human formulations the calcium concentration is likely to be slightly lower, providing an optimized Na/Ca ratio of 110-120. The Ioforminol formulations (2 ml/kg) were injected at a rate of 2 ml/s into a jugular vein, followed by a 20 ml saline flush at the same injection rate.

For comparison, Ioforminol at a concentration of 320 mg I/ml and 120 kVp tube voltage was administered to represent the current standard of care (SoC) imaging in man. SoC scans were compared to scans performed with either 60 or 200 mg I/ml contrast concentration in the same pig, with at least a 2 day washout period between each scanning session. Automated tube current modulation was used with a noise index level of 23 (SoC) and a tube rotation time of 0.7 s. Post-contrast CT images were acquired during the arterial phase, the portal venous phase, the venous phase and the late phase. Image reconstruction was done by (1) FBP, (2) ASiR 60% and (3) Veo. Pixel size was 0.703 mm×0.703 mm×2.5 mm.

Iodine contrast enhancement was assessed by measuring the mean x-ray attenuation values (in HUs) within circular region of interests (ROIs). ROIs were placed in both aorta and muscle (quadratus lumborum) in arterial phase images and in the liver in venous phase images. See Tables 1-6 and corresponding FIGS. 1-6. The aorta contrast to noise ratio (CNR) was calculated as the difference in signal between the aorta and muscle, divided by the noise in muscle. The liver signal to noise ratio (SNR) was calculated as the ratio of the mean liver attenuation and the standard deviation (SD).

Abbreviations Used:
SNR: Signal to noise ratio
CNR: Contrast to noise ratio
FBP: Filter back projection
ASiR: Adaptive statistical Iterative Reconstruction
SoC: Standard of Care

TABLE 1

Image acquisition and analysis data of arterial phase images covering aorta and muscle. CTDIvol: volume CT dose index following administration of Ioforminol at 320 mg I/ml (for comparison) and Ioforminol at 200 mg I/ml.

| Contrast Media concentration [mg I/ml] | Tube voltage [kVp] | Dose CTDI$_{vol}$ [mGy] | FBP [CNR] | ASiR 60% [CNR] | Veo [CNR] | FIG. 1 |
|---|---|---|---|---|---|---|
| Ioforminol 320 | 120 | 9.8 | 17.7 | | | A |
| Ioforminol 200 | 80 | 6.9 | 15.2 | | | B |
| Ioforminol 200 | 80 | 6.9 | | 23 | | C |
| Ioforminol 200 | 80 | 6.9 | | | 46.7 | D |

TABLE 2

Image acquisition and analysis data of arterial phase images covering aorta and muscle. CTDIvol: volume CT dose index following administration of Ioforminol at 320 mg I/ml (for comparison) and Ioforminol at 160 mg I/ml.

Figure 2:
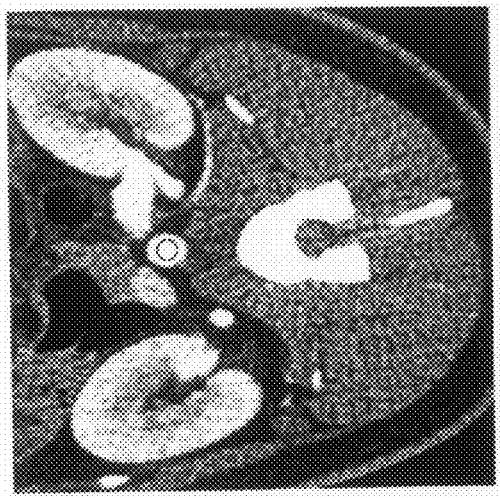
FIG. 2 shows images A to D using Ioforminol of 320 mg I/ml and 160 mg I/ml, and tube voltage energies of 120 and 80 KVp according to Table 2.
Figure 2:
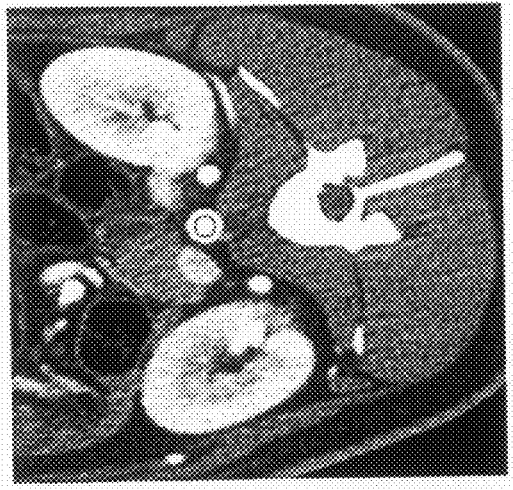
Figure 2:
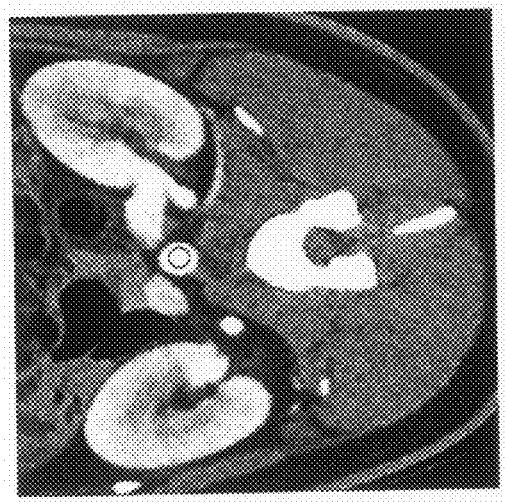
Figure 2:
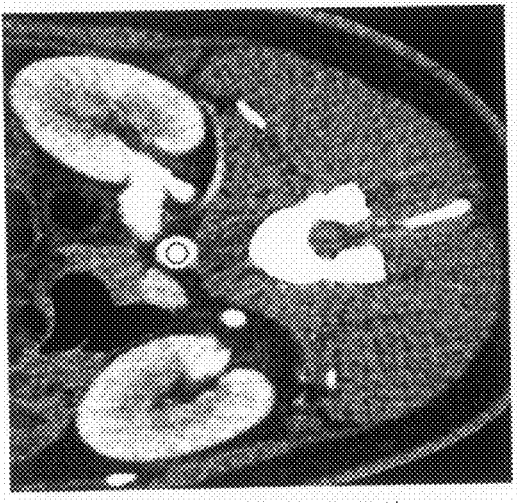

| Contrast Media concentration [mg I/ml] | Tube voltage [kVp] | Dose CTDI$_{vol}$ [mGy] | FBP [CNR] | ASiR 60% [CNR] | Veo [CNR] | FIG. 2 |
|---|---|---|---|---|---|---|
| Ioforminol 320 | 120 | 7.4 | 16.9 | | | A |
| Ioforminol 160 | 80 | 5.2 | 9.7 | | | B |
| Ioforminol 160 | 80 | 5.2 | | 15.1 | | C |
| Ioforminol 160 | 80 | 5.2 | | | 32.1 | D |

TABLE 3

Image acquisition and analysis data of arterial phase images covering aorta and muscle. CTDIvol: volume CT dose index following administration of Ioforminol at 320 mg I/ml (for comparison) and Ioforminol at 200 mg I/ml.

Figure 3:
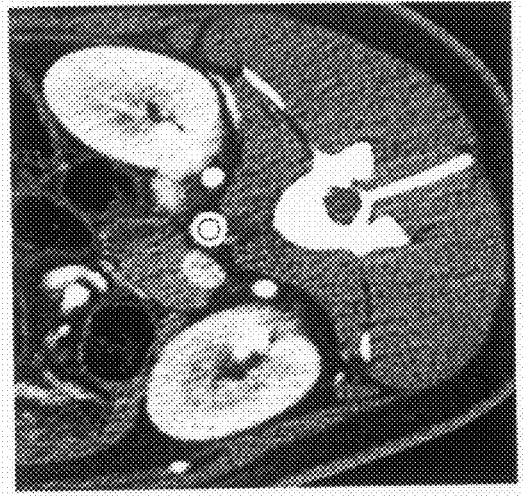
FIG. 3 shows images A to D using Ioforminol of 320 mg I/ml and 200 mg I/ml, and tube voltage energies of 120 and 100 KVp according to Table 3.
Figure 3:
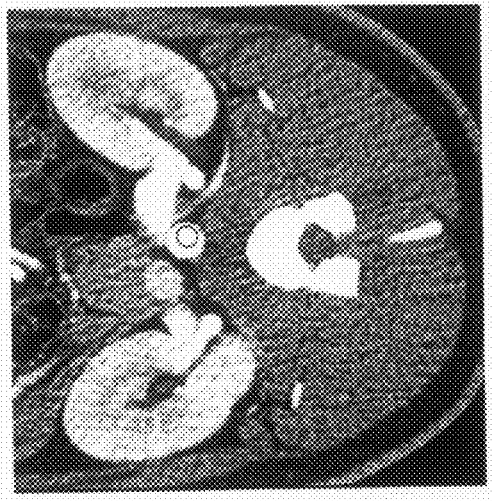
Figure 3:
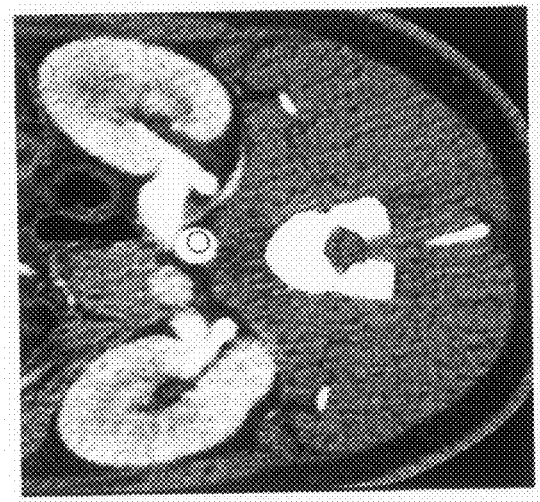
Figure 3:
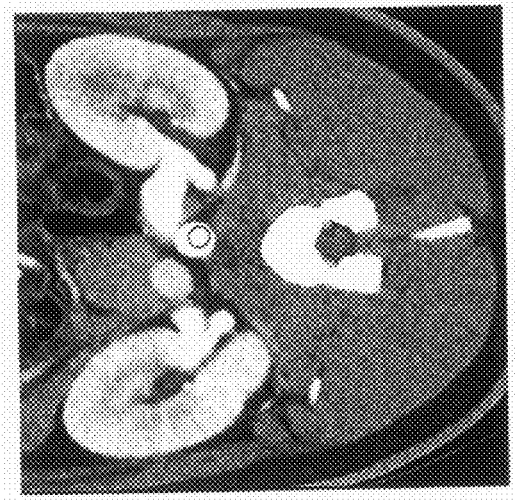

| Contrast Media concentration [mg I/ml] | Tube voltage [kVp] | Dose CTDI$_{vol}$ [mGy] | FBP [CNR] | ASiR 60% [CNR] | Veo [CNR] | FIG. 3 |
|---|---|---|---|---|---|---|
| Ioforminol 320 | 120 | 7.4 | 16.9 | | | A |
| Ioforminol 200 | 100 | 5.2 | 11.7 | | | B |
| Ioforminol 200 | 100 | 5.2 | | 17.7 | | C |
| Ioforminol 200 | 100 | 5.2 | | | 33.2 | D |

TABLE 4

Image acquisition and analysis data of venous phase images covering liver. CTDIvol: volume CT dose index following administration of Ioforminol at 320 mg I/ml (for comparison) and Ioforminol at 200 mg I/ml.

Figure 4:
FIG. 4 shows images A to D using Ioforminol of 320 mg I/ml and 200 mg I/ml, and tube voltage energies of 120 and 80 KVp according to Table 4.
Figure 4:
Figure 4:
Figure 4:

| Contrast Media concentration [mg I/ml] | Tube voltage [kVp] | Dose CTDI$_{vol}$ [mGy] | FBP [SNR] | ASiR 60% [SNR] | Veo [SNR] | FIG. 4 |
|---|---|---|---|---|---|---|
| Ioforminol 320 | 120 | 9.8 | 7.7 | | | A |
| Ioforminol 200 | 80 | 6.9 | 6.4 | | | B |
| Ioforminol 200 | 80 | 6.9 | | 9.5 | | C |
| Ioforminol 200 | 80 | 6.9 | | | 16.7 | D |

TABLE 5

Image acquisition and analysis data of venous phase images covering liver. CTDIvol: volume CT dose index following administration of Ioforminol at 320 mg I/ml and Ioforminol at 160 mg I/ml.

Figure 5:
FIG. 5 shows images A to D using Ioforminol of 320 mg I/ml and 160 mg I/ml, and tube voltage energies of 120 and 80 KVp according to Table 5.
Figure 5:
Figure 5:
Figure 5:

| Contrast Media concentration [mg I/ml] | Tube voltage [kVp] | Dose CTDI$_{vol}$ [mGy] | FBP [SNR] | ASiR 60% [SNR] | Veo [SNR] | FIG. 5 |
|---|---|---|---|---|---|---|
| Ioforminol 320 | 120 | 7.4 | 8.2 | | | A |
| Ioforminol 160 | 80 | 5.2 | 4.6 | | | B |

TABLE 5-continued

Image acquisition and analysis data of venous phase images covering liver. CTDIvol: volume CT dose index following administration of Ioforminol at 320 mg I/ml and Ioforminol at 160 mg I/ml.

| Contrast Media concentration [mg I/ml] | Tube voltage [kVp] | Dose CTDI$_{vol}$ [mGy] | FBP [SNR] | ASiR 60% [SNR] | Veo [SNR] | FIG. 5 |
|---|---|---|---|---|---|---|
| Ioforminol 160 | 80 | 5.2 | | 7.7 | | C |
| Ioforminol 160 | 80 | 5.2 | | | 15.1 | D |

TABLE 6

Image acquisition and analysis data of venous phase images covering liver. CTDIvol: volume CT dose index following administration of Ioforminol at 320 mg I/ml (for comparison) and Ioforminol at 200 mg I/ml.

Figure 6:
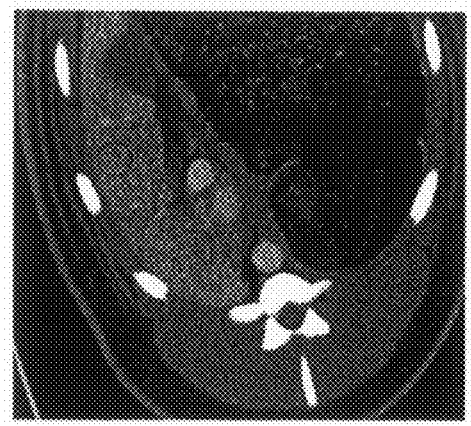
FIG. 6 shows images A to D using Ioforminol of 320 mg I/ml and 200 mg Um', and tube voltage energies of 120 and 100 KVp according to Table 6.
Figure 6:
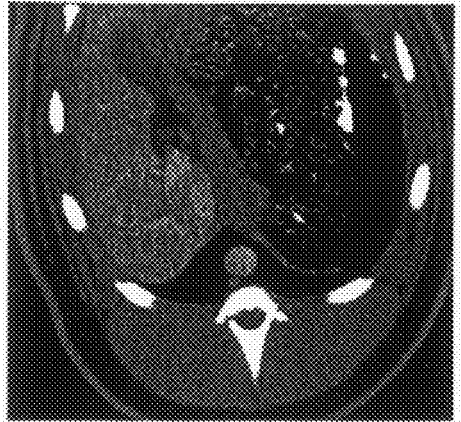
Figure 6:
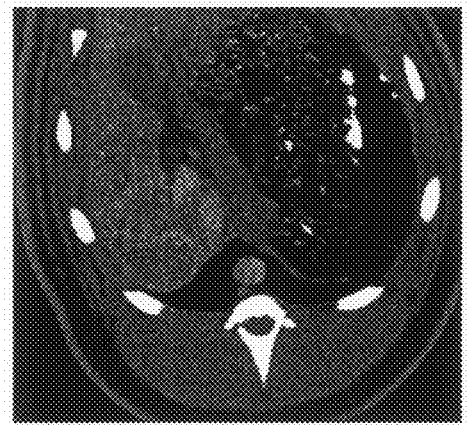
Figure 6:
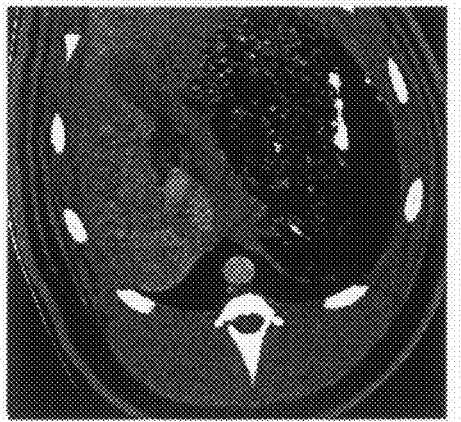

| Contrast Media concentration [mg I/ml] | Tube voltage [kVp] | Dose CTDI$_{vol}$ [mGy] | FBP [SNR] | ASiR 60% [SNR] | Veo [SNR] | FIG. 6 |
|---|---|---|---|---|---|---|
| Ioforminol 320 | 120 | 7.4 | 8.2 | | | A |
| Ioforminol 200 | 100 | 5.2 | 5.1 | | | B |
| Ioforminol 200 | 100 | 5.2 | | 7.9 | | C |
| Ioforminol 200 | 100 | 5.2 | | | 13.1 | D |

When the concentration of Ioforminol is reduced to 200 mg I/ml and kVp reduced to 80 and 60% ASIR is used, the CNR is maintained at 23 in the arterial phase. This is in comparison to 17.7 for the SoC (Ioforminol 320 mg I/ml and 120 kVp with FBP). When Veo is used, the CNR is increased to 46.7, largely because the background noise is reduced to a greater extent (FIG. 1). Similarly in the venous phase when concentration of Ioforminol is reduced to 200 mg I/ml and kVp reduced to 80 and 60% ASIR is used, the CNR is maintained at 9.5. This is in comparison to 7.7 for the SoC (Ioforminol 320 mg I/ml and 120 kVp with FBP). When Veo is used the CNR is increased to 16.7, largely because the background noise is reduced to a greater extent (FIG. 4).

When concentration of Ioforminol is reduced further to 160 mg I/ml and kVp reduced to 80 and 60% ASIR is used, the CNR is maintained at 15.1 in the arterial phase. This is in comparison to 16.9 for the SoC (Ioforminol 320 mg I/ml and 120 kVp with FBP). When Veo is used, the CNR is increased to 32.1, largely because the background noise is reduced by over 50% (FIG. 2). Similarly in the venous phase when the concentration of Ioforminol is reduced to 160 mg I/ml and kVp reduced to 80 and 60% ASIR is used, the CNR is maintained at 7.7. This is in comparison to 8.2 for the SoC (Ioforminol 320 mg I/ml and 120 kVp with FBP). When Veo is used the CNR is increased to 15.1, largely because the background noise is reduced to a greater extent (FIG. 5).

In a third setting when concentration of Ioforminol is reduced to 200 mg I/ml and kVp reduced to 100 and 60% ASIR is used, the CNR is maintained at 17.7 in the arterial phase. This is in comparison to 16.9 for the SoC (Ioforminol 320 mg I/ml and 120 kVp with FBP). When Veo is used, the CNR is increased to 33.2, largely because the background noise is reduced to a greater extent (FIG. 3). Similarly in the venous phase when concentration of Ioforminol is reduced to 200 mg I/ml and kVp reduced to 100 and 60% ASIR is used, the CNR is maintained at 7.9. This is in comparison to 8.2 for the SoC (Ioforminol 320 mg I/ml and 120 kVp with FBP). When Veo is used the CNR is increased to 13.1, largely because the background noise is reduced to a greater extent (FIG. 6).

Conclusions: A similar image quality in terms of CNR is observed with a reduced tube current of 80 kVp (compared to SoC setting of 120 kVp) and ASIR 60% (compared to standard SoC FBP method) when at the same time reducing iodine contrast concentration to 200 or 160 mg I/mL and reducing radiation dose by ~30% compared to the SoC setting.

Extrapolation to the Clinical Setting:

These data suggest that, given a relationship between the concentration of injected iodinated contrast agent and the concentration appearing in blood vessels during clinical angiographic CT procedures, the injected (concentration in vial) concentration may be reduced from standard concentrations e.g. from 320 mg I/ml to between 200 mg I/ml and 160 mg I/ml when kVp is reduced to 100 and 80 kVp. It follows that, if the volumes of injected iodinated contrast agent remain the same and the concentration of iodine based contrast agent is reduced, the total amount of injected iodinated contrast agent into the body will be reduced. This reduction in overall amount of iodinated contrast agent would have fewer side effects for the infant, child and adult patient and confer significant patient safety benefits, especially those subjects with immature kidneys, or those who would be susceptible potential adverse events such as to iodinated contrast agent-induced major adverse cardiac events, renal dysfunction or contrast media induced acute kidney injury.

Furthermore, the respective reduction in radiation dose levels concomitant with maintained or increased CNR/SNR suggest lower radiation levels are simultaneously possible. Since exposure to radiation at an early age carries a risk to organs and tissues a lower radiation exposure would be of considerable additional benefit in these subjects, especially the young.

Example 2: Comparison of Injection Pressure for Ioforminol of Different Iodine Concentrations Two target iodine concentrations were investigated; 160 mg I/ml and 200 mg I/ml. In this study, Ioforminol was formulated at these specific concentrations and the standard concentration (320 mg I/ml), for comparison. For each experiment, Göttingen mini pigs received a fixed contrast agent volume (2 ml/kg, ~80 ml) injected into the vena cava superior, via port-a-cath unit (Power PAC II, 1.9 mm, Smiths Medical, Zaventem, Belgium) placed subcutaneously at the level of the left shoulder, at a fixed injection rate (2 ml/s). Hence the use of different iodine contrast concentrations resulted in different iodine delivery rates (IDR) and total iodine doses (TID). Table 7 summarizes the investigated injection protocols. The contrast agent injection was always followed by a fixed saline chaser of 20 ml at the same injection rate as the contrast.

TABLE 7

Injection protocol details.

| Contrast concentration (mg I/ml) | Injection volume (ml/kg) | Injection rate (ml/s) | Iodine delivery rate (g I/s) | Total iodine dose (mg I/kg) |
|---|---|---|---|---|
| 320 | 2 | 2 | 0.64 | 640 |
| 200 | 2 | 2 | 0.40 | 400 |
| 160 | 2 | 2 | 0.32 | 320 |

Figure 7:
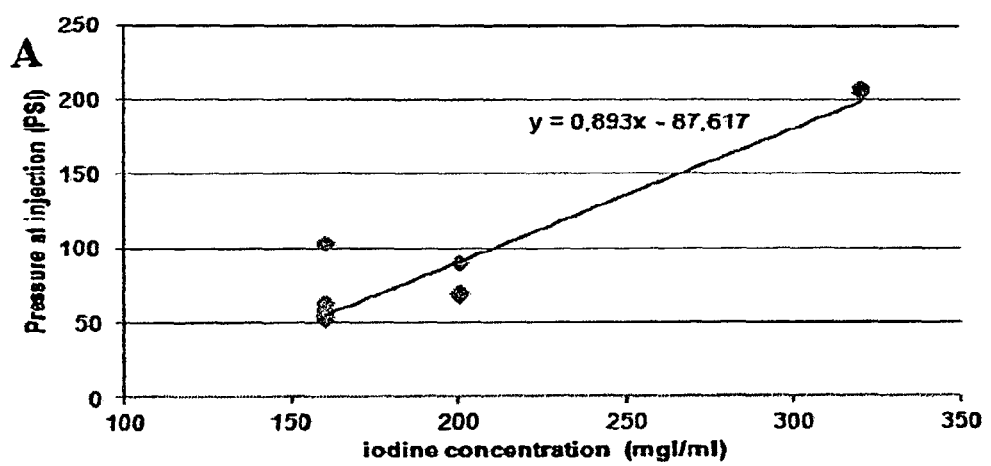
FIG. 7 shows the injection pressure versus concentration when injecting Ioforminol of various iodine concentrations.

Contrast agent compositions were injected at room temperature (20° C.) using a dual head injector (Nemoto- Kyorindo, Tokyo, Japan). The injection pressure was monitored during each injection protocol. A linear relation was observed between the peak pressure and the iodine contrast concentration, as shown in FIG. 7, providing the injection pressure versus concentration.

The obtained data indicate that the lower viscosities of the 160 and 200 mg I/ml Ioforminol compositions compared with the 320 mg I/ml composition have an advantage that the compositions are easy to administer. These lower concentrations may therefore be more compatible with handheld syringes. Further, it should be easier to use thinner cannulas or catheters with less risk of extravasation, which is particularly favourable in pediatrics and elderly patients, providing a more patient friendly contrast media administration protocol.

What is claimed is:

1. An X-ray composition comprising Ioforminol and a pharmaceutically acceptable carrier or excipient, wherein the composition comprises an iodine concentration of 40-170 mg I/ml, a sodium ion concentration of 70-120 mM, a calcium ion concentration of 0.5-1.3 mM, and a ratio between the sodium ion and the calcium ion in the range between 110 and 120.

2. A composition as claimed in claim 1, wherein the iodine concentration is 80-130 mg I/ml, a sodium ion concentration of 88-100 mM, and a calcium ion concentration of 0.7-0.9 mM.

3. A composition as claimed in claim 1, further comprising potassium and/or magnesium ions.

4. A composition as claimed in claim 1, wherein the total volume of the composition for administration to a living subject is between 1 and 250 ml.

5. A composition as claimed in claim 1, wherein the iodine concentration is about 160 mg I/ml, the sodium concentration is about 82 mM, and having a calcium concentration of 0.7 mM.

6. A method of x-ray examination, the method comprising administering the composition of claim 1 to a living subject,
applying an X-ray radiation dose to the living subject,
examining the living subject with a diagnostic device and compiling data from the examination.

7. A method as claimed in claim 6, wherein said dose of radiation has an average energy spectrum substantially corresponding to the k-edge of iodine.

8. A method as claimed in claim 6, wherein the X-ray radiation dose is provided by a tube voltage energy in the range of 70-140 kVp.

9. A method as claimed in claim 6, wherein the X-ray radiation dose is provided by a tube current in the range of 5-1000 mA.

10. A method as claimed in claim 6, further including a step of noise reduction through an advanced image reconstruction method.

11. A method as claimed in claim 6, wherein the noise reduction is selected from the iterative image reconstruction methods ASiR and MBIR.

12. A method as claimed in claim 6, including Dual Energy CT.

13. A method of x-ray examination, the method comprising administering an X-ray composition to a living subject,
wherein the composition comprising Ioforminol having an iodine concentration of 80-130 mg I/ml, a sodium ion concentration of 88-100 mM, and a calcium ion concentration of 0.7-0.9 mM, a ratio between the sodium ion and the calcium ion in the range between 110 and 120, and a pharmaceutically acceptable carrier or excipient, the method comprising,
applying an X-ray radiation dose to the living subject,
examining the living subject with a diagnostic device and compiling data from the examination,
wherein said dose of radiation has an average energy spectrum substantially corresponding to the k-edge of iodine.

14. A method as claimed in claim 13, wherein the X-ray radiation dose is provided by a tube voltage energy in the range of 70-140 kVp.

15. A method as claimed in claim 13, wherein the X-ray radiation dose is provided by a tube current in the range of 5-500 mA.

16. A method as claimed in claim 13, further including a step of noise reduction through an advanced image reconstruction method.

17. A method as claimed in claim 13, wherein the noise reduction is selected from the iterative image reconstruction methods ASiR and MBIR.

18. A method as claimed in claim 13, including Dual Energy CT.

19. A method as claimed in claim 13, wherein the X-ray radiation dose is provided by a tube voltage energy in the range of about 80 kVp and the volume of the composition is about 1.5 mL/kg of the living subject.

* * * * *